United States Patent [19]
Brown et al.

[11] Patent Number: 4,944,942
[45] Date of Patent: Jul. 31, 1990

[54] INTRANASAL VACCINATION OF HORSES WITH INACTIVATED MICROORGANISMS OR ANTIGENIC MATERIAL

[75] Inventors: Karen K. Brown, Kansas City, Mo.; Sharon A. Bryant, Shawnee, Kans.

[73] Assignee: Mobay Corporation, Pittsburgh, Pa.

[21] Appl. No.: 90,272

[22] Filed: Aug. 27, 1987

[51] Int. Cl.$^5$ .................... A61K 39/09; A61K 39/12
[52] U.S. Cl. ......................................... 424/89; 424/92
[58] Field of Search ................................. 424/89, 92

[56] References Cited

U.S. PATENT DOCUMENTS

| 3,852,420 | 12/1974 | Usdin | 424/92 |
|---|---|---|---|
| 4,500,513 | 2/1985 | Brown et al. | 424/89 |
| 4,582,798 | 4/1986 | Brown et al. | 435/68 |

FOREIGN PATENT DOCUMENTS 0230264  7/1987  European Pat. Off. .

OTHER PUBLICATIONS

Polly et al., Journal of Infectious Diseases, vol. 131, No. 3, pp. 217-224, Human Strept Vaccine Aerosol Spray, Protective Studies with a Group A Streptococcal M. Protein Vaccine, Mar. 1975.

D'Alessandri, Journal of Infectious Diseases, vol. 138, No. 6, Dec. 1978, pp. 712-718, Protective Studies with Group A Streptococcal M. Protein Vaccine, Human Nasal Strept Vaccine.

Galan et al, Infection & Immunity, vol. 47, No. 3, pp. 623-628, Mar. 1985, S. equi in Horses Locally, Mucosal Nasopharyngeal Immune Responses of Horses to Protein Antigens.

I. Van de Rijn, pp. 444-448, vol. 27 (Feb. 1980) of Infection and Immunity.

American Journal of Veterinary Research, 41(2): Feb. 1980, by J. M. Cummins and B. Rosenquist, Protection of Calves Against Rhinovirus Infection by Nasal Secretion Interferon Induced by Infectious Bovine Rhinotracheitis Virus, pp. 161-165.

Commonwealth Agricultural Bureau, 1986, NR. 86162129; J. F. Timoney et al.: "The Protective Response of the Horse to an Avirulent Strain of Stroptococcus equi", & Coll. Vet. Med., Cornell Univ., Ithaca, NY 14853.

Chemical Abstracts, Band 72, 1970 Seite 179 Zusammenfassung NR. 98582a, Columbus, Ohio, U.S.; B. T. Rouse et al; "Response of Ponies to Myxovirus Influenza A-equi 2. I. Serum and Nasal Antibody Titers Following Exposure", & Can. J. Comp. Med., 1970, 34(1), 1-6.

Primary Examiner—Ronald W. Griffin
Attorney, Agent, or Firm—Joseph C. Gil; Lyndanne M. Whalen

[57] ABSTRACT

Horses can be immunized by the intranasal administration of antigenic material which provokes the proliferation of antibodies which reduce or neutralize the virulence of invasive microorganisms. These antigenic materials may be inactivated whole organisms, extracts from such organisms, or recombinant DNA or synthetic peptide antigens. This antigenic material can be combined with adjuvants and transdermal carriers or it can just be carried in sterile water. The intranasal vaccination may be part of a total regimen that includes other routes of administration such as intramuscular injection.

19 Claims, 6 Drawing Sheets

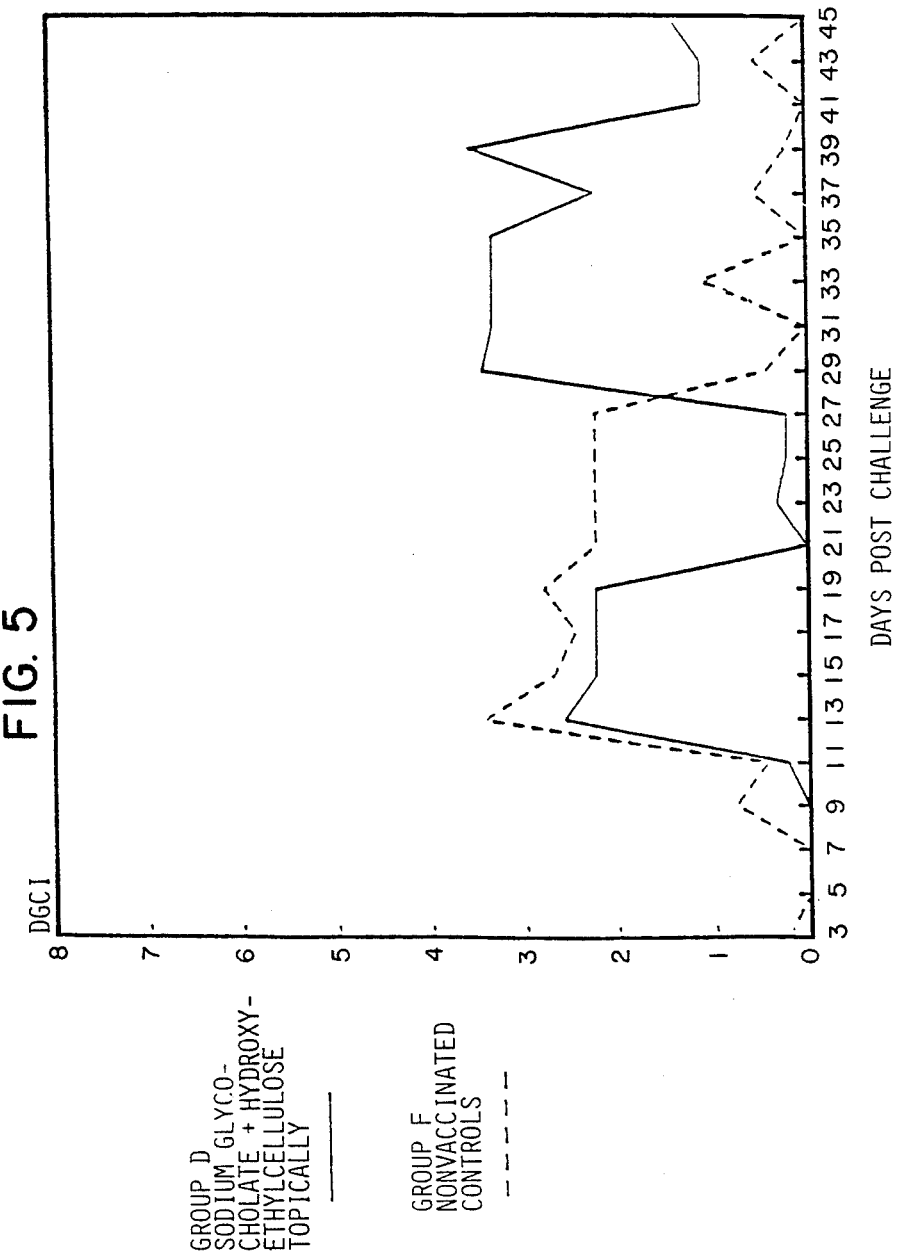

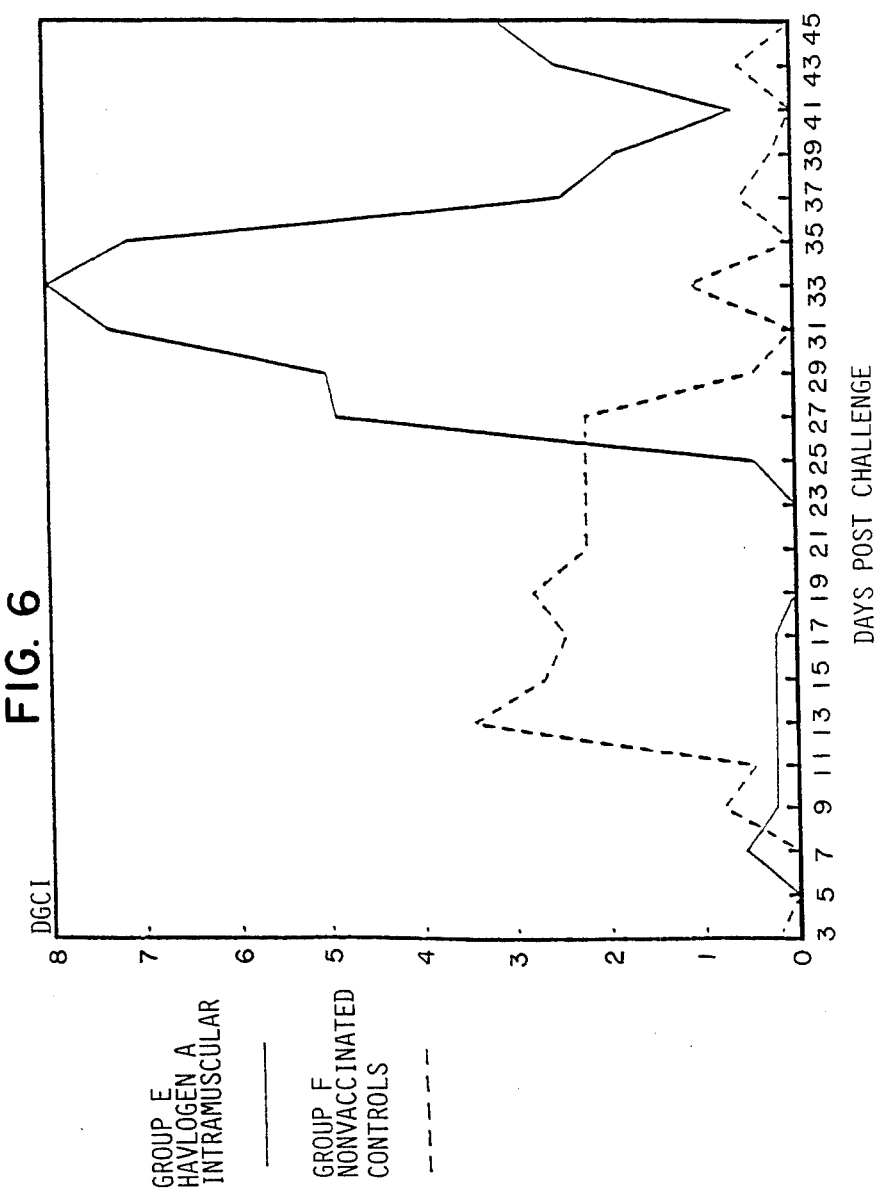

INTRANASAL VACCINATION OF HORSES WITH INACTIVATED MICROORGANISMS OR ANTIGENIC MATERIAL

BACKGROUND OF THE INVENTION

The two basic problems of immunizing against disease by vaccination are isolation of an antigen which is capable of provoking the production of protective antibodies, i.e. antibodies which inhibit or impair the ability of the disease causing organism to invade the host animal, and the presentation of this immunity provoking antigen to the hose animal in a way which actually stimulates production of the protective antibodies which confer immunity or partial immunity. Historically, the earliest efforts at immunization have involved the entire disease causing organism which was either killed or substantially weakened. In some cases the causative organism was not even separated from the medium in which it was obtained, the most famous example being the development of rabies vaccine by Pasteur. In many cases these "whole culture" vaccines caused undesirable side reactions. Thus more recent efforts have been directed toward isolating those molecules of the causative organisms which provoke the production of the appropriate antibodies.

This general development sequence was indeed followed in the case of vaccines against Streptococcus equi invasion of horses. The initial vaccine was comprised of killed whole cells but provoked undesirable side reactions which are detailed in the background discussion of U.S. Pat. No. 3,852,420. This patent is concerned with extracting an immunity provoking antigen by hot acid treatment of cells of this organism. However, this extract still contained extraneous materials which caused some undesirable side reactions such as swelling at the site of injection. U.S. Pat. No. 4,582,798 is concerned with an alternative technique for extracting the antigen of interest by treatment of the cells with mutanolysin and an anionic detergent. This technique yields an extract which causes an even further reduced incidence of side reactions.

The initial manner of presenting the antigenic material, whether the whole organism or an extract, was by introduction into the circulatory system of the host animal. Indeed it had been felt that the development of circulating antibodies, which was best accomplished by introduction of the antigenic material into the circulatory system, was critical to the development of immunity. Subsequently, it was found that in some cases immunity can be induced by localized introduction of antigenic material. For instance, the article "Protective Studies with a Group A Streptococcal M Protein II Challenge of Volunteers after Local Immunization in the Upper Respiratory Tract" by S. M. Polly, R. H. Waldman, P. High, M. K. Wittner, A. Dorfman and E. H. Fox at pages 217 to 224 of Volume 131, Number 3 (March 1975) of *The Journal of Infectious Diseases* reports on the immunization of humans against clinical illness induced by a class of microorganisms by the administration of an aerosol spray containing the appropriate antigen into the nose and oropharynx. In a follow up study the response to subsequent challenge by virulent organisms was compared to that of individuals vaccinated by subcutaneous injection and to that of unvaccinated individuals. The aerosol administration gave a measure of protection and provoked fewer and less severe side reactions than the parenteral injection route (see "Protective Studies with Group A Streptoccal M Protein Vaccine III Challenge of Volunteers after Systemic or Internal Immunization with Type 3 or Type 12 Group A Streptococcus") by R. D'Alessandri, G. Plotkin, R. M. Kluge, M. K. Wittner, F. N. Fox, A. Dorfman, and R. H. Waldman in *The Journal of Infectious Diseases*, Volume 138, number 6 (December 1978).

In the case of *Streptococcus equi* the presentation of the immunity provoking antigen has been by intramuscular injection of the target equines. In the case of the antigens extracted by acid or enzyme the injected vaccine has included an adjuvant to enhance the antibody response. These adjuvants were felt necessary to obtain a sufficient antibody response to reduce or suppress the symptoms on subsequent challenge with the virulent organism. It was felt that the slow release of antigen extract from the adjuvant into the blood stream of the vaccinated horse was critical to obtaining an adequate level of immunity.

A recent study has suggested that the antibodies generated locally at the site of invasion may be more significant than serum antibodies (those antibodies found generally in the circulatory system) for *Streptococcus equi* infections in the horse. In "Mucosal Nasopharyngeal Immune Response of Horses to Protein Antigens of *Streptococcus equi*" by J. E. Galon and J. F. Timeney at pages 623 to 628 of volume 47, number 3 (March 1985) of *Infection and Immunity* it is reported that the correlation between serum antibodies and field protection is rather poor and that locally generated antibodies recognized antigens not recognized by the serum antibodies. It is further hypothesized that neutralization of these antigens may be important in obtaining protection. However, intranasal vaccination was neither suggested nor attempted. Rather some ponies were given intramuscular injections of aluminum hydroxide adjuvanted acid extract of *Streptococcus equi* and then these vaccinates and unvaccinated control ponies were challenged by intranasal spraying of virulent organisms. All of the challenged ponies developed illness ("strangles") but were resistant to infection on rechallenge.

The intranasal vaccination of horses with killed bacteria (bacterins) or antigenic extracts presents special problems. It has not been established that such a route could actually provide any degree of immunity. Conventional wisdom has been that only a modified live vaccine could be effectively administered in this manner because only such a preparation would present an adequate concentration of antigen. Indeed some work with intranasal vaccination with influenza virus has been reported in U.S. Pat. No. 4,500,513. Furthermore, the delivery of the vaccine presents special problems because of the structure of the horse's nose. The vaccine should be delivered to the tonsilor tissue which is typically some 12 to 14 inches (30 to 35 cm) back from the nasal orifice. The normal technique for nasal application is by atomized spray as detailed in the D'Alessandri and Polly articles discussed hereinabove. However, delivery of an adequate dose into a horse's nose would require approximately five minutes and horses have virtually no tolerance for the hissing noise associated with such atomizers. It is believed that previous horse challenges such as that reported in the Galan article discussed hereinabove were conducted by sedating the animals before subjecting them to the atomized spray.

BRIEF DESCRIPTION OF THE DRAWINGS

FIG. 5 is a graph of Daily Group Clinical Indices versus days post challenge for unvaccinated horses and horses vaccinated topically with Formulation 4.

FIG. 6 is a graph of Daily Group Clinical Indices versus days post challenge for unvaccinated horses and horses vaccinated intramuscularly with Formulation 3.

SUMMARY OF THE INVENTION

Figure 1:
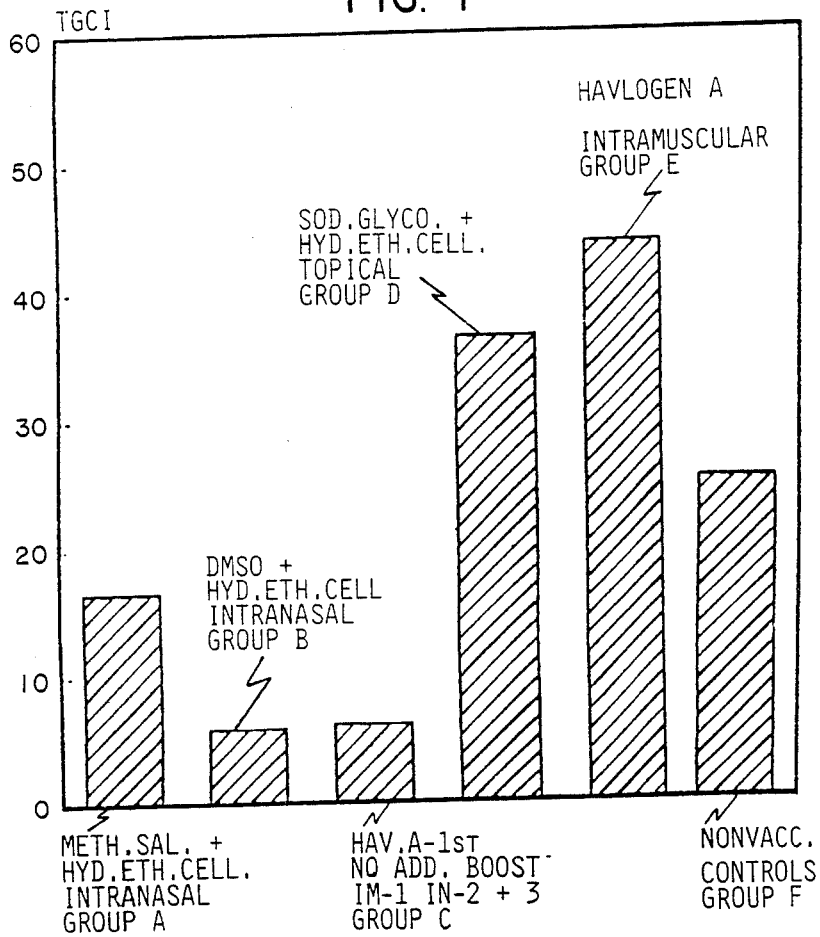
FIG. 1 is a bar graph illustrating the effects of various vaccine formulations on the Total Group Clinical Indices which measure the symptomatic response of horses to challenge by virulent organisms.
Figure 2:
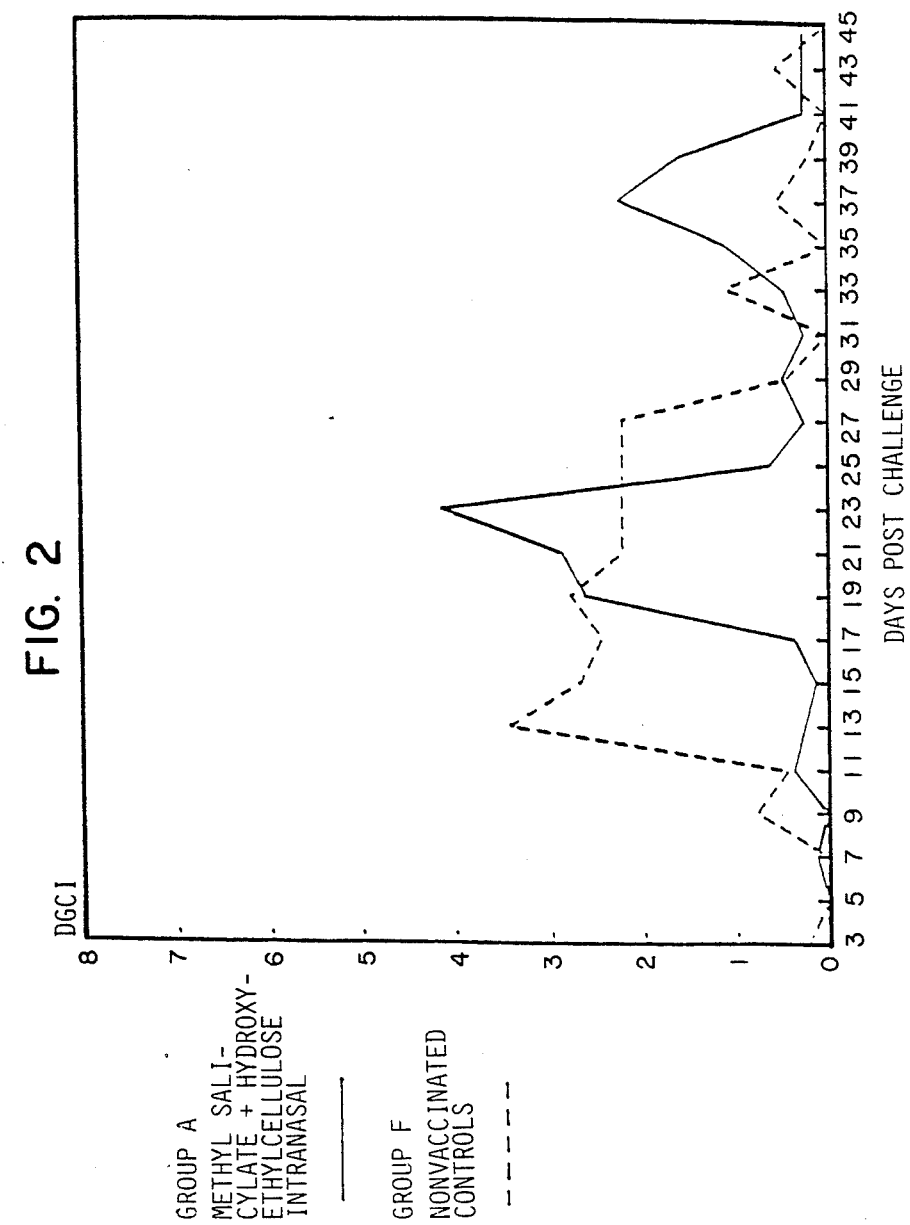
FIG. 2 is a graph of Daily Group Clinical Indices versus days post challenge for unvaccinated horses and horses vaccinated intranasally with Formulation 1.
Figure 3:
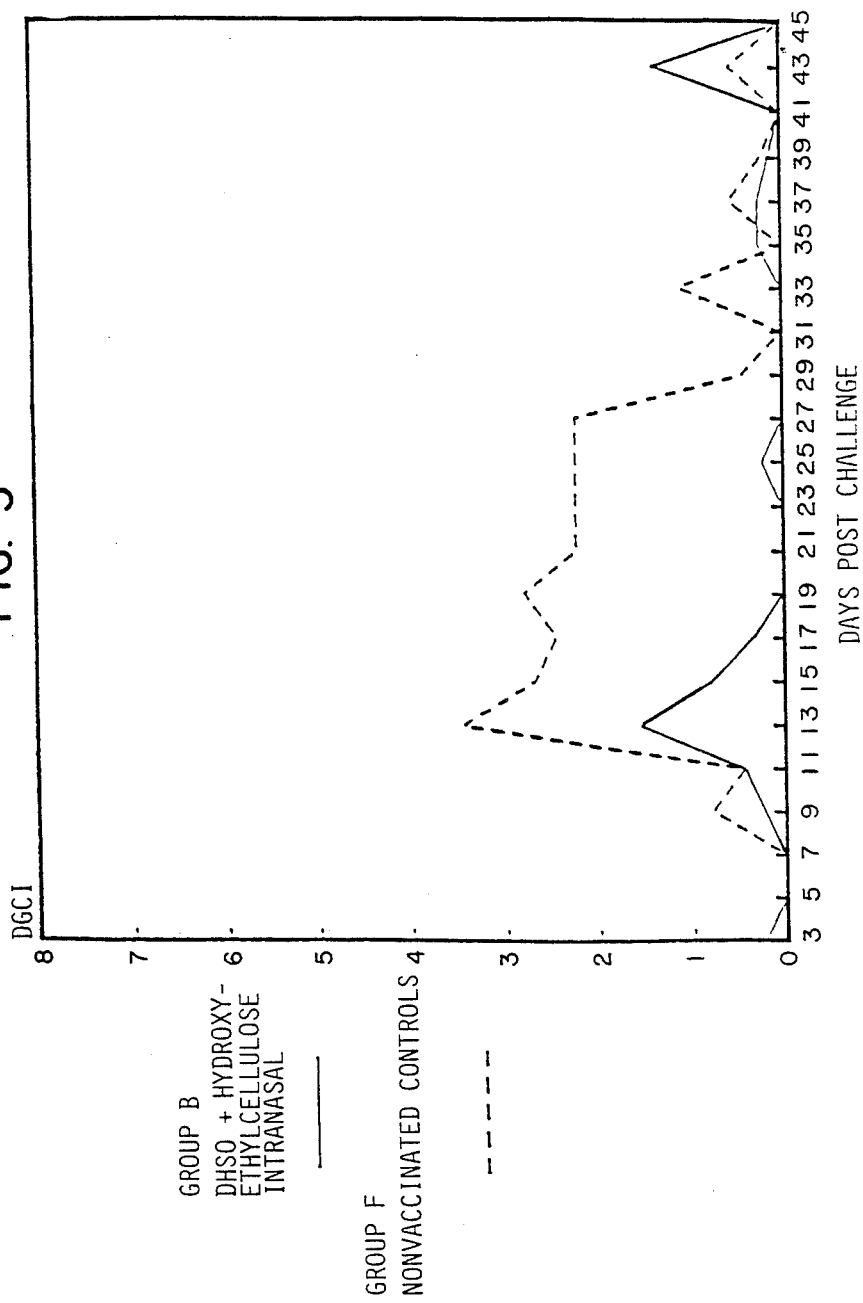
FIG. 3 is a graph of Daily Group Clinical Indices versus days post challenge for unvaccinated horses and horses vaccinated intranasally with Formulation 2.
Figure 4:
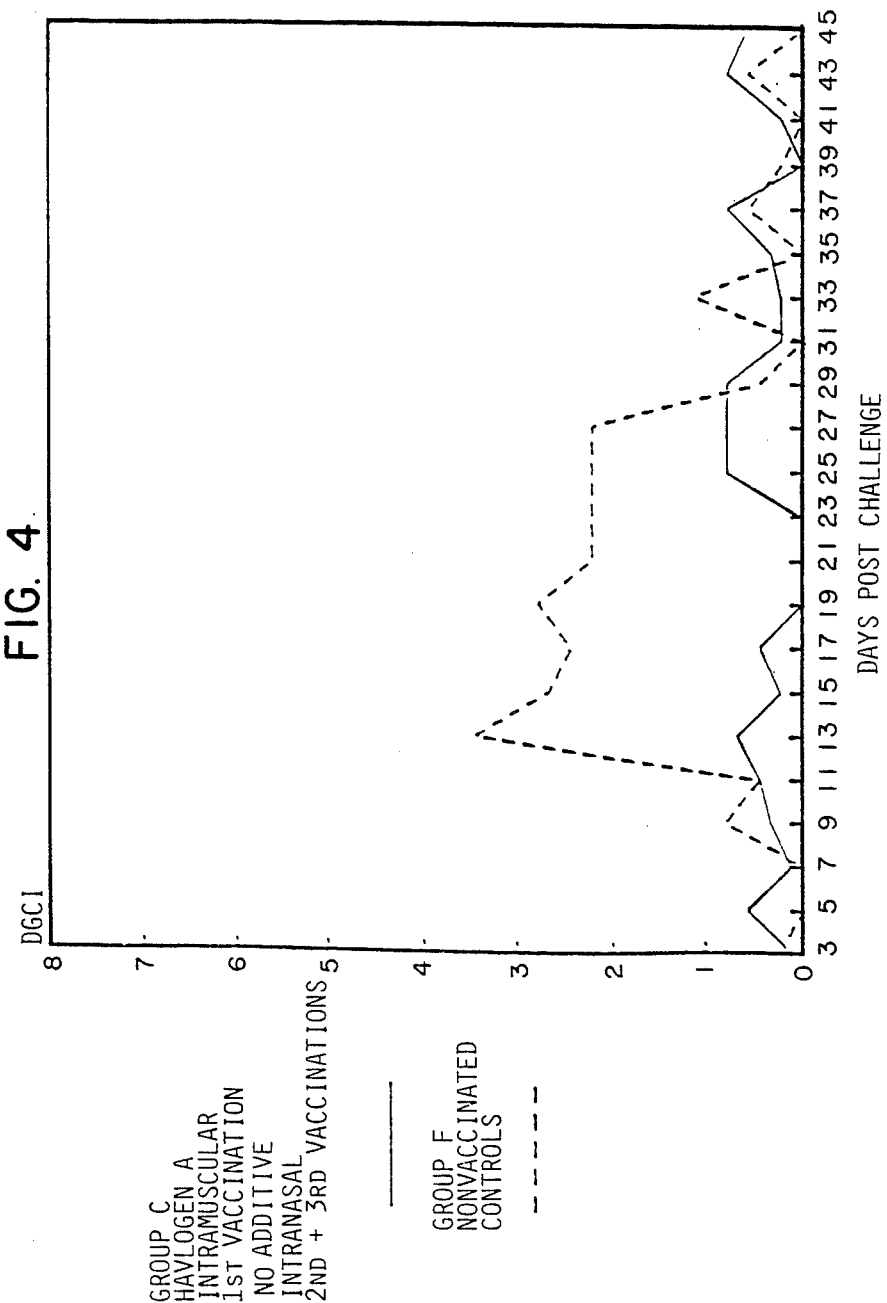
FIG. 4 is a graph of Daily Group Clinical Indices versus days post challenge for unvaccinated horses and horses vaccinated intramuscularly with Formulation 3 and intranasally with Formulation 5.

It has been discovered that horses can be immunized against microbiological infection by the application of killed organisms or antigenic extracts to their nasal mucosal and tonsilor tissue. The vaccine can conveniently be incorporated into an appropriate liquid carrier and sprayed as a liquid stream onto the walls of the nose in the vicinity of the tonsilor tissue. This technique is particularly effective for respiratory diseases of horses such as *Streptococcus zooepidemicus, Streptococcus equisimilis* and *Streptococcus equi*, especially the last.

DETAILED DESCRIPTION OF THE INVENTION

The antigenic material utilized in the present invention can be inactivated whole organisms or appropriate extracts prepared from such organisms (subunits), recombinant DNA derived antigen or synthetic peptide antigen. The antigenic material is preferably derived from a bacteria which causes respiratory disease in the horse, is more preferably derived from a Group C Streptoccal organism such as *Streptococcus zooepidemicus* and *Streptococcus equi*, most preferably from the latter. However, it may also be killed virus such as equine influenza or other disease causing microorganisms. Thus the antigenic material can be derived from any microorganism whose virulence in horses is neutralized by antibodies of the equine secretory systems. It may also be a combination such as killed virus of the Miami and Pennsylvania strains of equine influenza with an antigen (enzyme extract, hot acid extract or other) of *Streptococcus equi*.

This antigenic material is preferably an extract which contains antigenic determinants which provoke the proliferation of neutralizing antibodies. In the case of *Streptococcus equi* U.S. Pat. No. 3,852,420 teaches an appropriate acid extraction technique and U.S. Pat. No. 4,582,798 teaches an appropriate enzyme extraction technique. The latter technique can also be applied to cultures of *Streptococcus zooepidemicus*.

The present administration technique allows the utilization of antigenic materials which display objectionable reactivity in other administration routes. For example the Streptococcal organisms are known to have a high affinity for dermal tissue and vaccines prepared with killed cells or some extracts cause swelling and other irritation at the site of injection. Similar reactivity is not observed with intranasal administration. Killed whole cell suspensions of *Streptococcus equi* grown in both Todd Hewitt broth and chemically defined media free of protein were administered intranasally without provoking any noticeable reaction. The former material was reported in U.S. Pat. No. 3,852,420 to give substantial reactions upon parenteral injection.

The preferred technique for preparing antigenic material effective against *Streptococcus equi* is by enzyme extraction such as with pepsin. It is particularly preferred to use a bacteriolytic enzyme such as lysozyme or mutanolysin. It is particularly preferred to utilize mutanolysin. It is also preferred to follow the enzyme extraction with extraction with an anionic detergent such as sodium dodecyl sulfate. It is particularly advantageous to grow the *Streptococcus equi* to be extracted in a protein free chemically defined medium such as that described in the article by I. Van de Rijn at pages 444 to 448 of Volume 27 (1980) of *Infection and Immunity*.

The antigenic material can be formulated for application in a variety of ways. It can be simply dispersed or dissolved in sterile water or carriers or thickening agents and adjuvants can be added to the water. A preferable formulation includes thickening agents, especially those derived from cellulose such as the semi-synthetic cellulose derivatives including carboxymethylcellulose, hydroxypropylcellulose and most especially hydroxyethylcellulose. These thickening agents may have viscosities as two weight percent solutions in water between about 100 and 100,000 cps, preferably between about 100 and 10,000 cps and most preferably between about 1000 and 8000 cps. In the hydroxyethylcelluloses this implies intrinsic viscosity determined molecular weights between about 80,000 and 1,200,000. It is particularly preferred to use a hydroxyethylcellulose which has been ethoxylated with about 2.5 moles of ethylene oxide per mole of anhydrogluclose unit. Such thickening agents are preferably present in amounts between about 0.25 and 1 weight percent based on the total formulation. Dermal penetrants such as dimethyl sulfoxide (DMSO) and methyl salicylate are also preferably included. Particularly advantageous amounts lie between about 0.5 and 10 weight percent based upon the total formulation depending on the particular penetrant utilized. For instance, with DMSO the preferred range is between about 2.5 and 10 weight percent while with methyl salicylate the preferred range is between 1 and 4 weight percent. Finally, the formulation may contain a recognized vaccine adjuvant such as aluminum hydroxide gel or those taught in U.S. Pat. No. 3,919,411, preferably at levels between about 5 and 40% by volume with levels between about 10 and 40% by volume especially preferred for the former type and levels between about 5 and 20% being preferred for the latter type. An especially preferred adjuvant is based on the polyacrylic acid cross linked with polyallyl sucrose sold as Carbopol 934P combined with polyoxyethylene sorbitan mono-oleate and sorbitan monolaurate and is preferably used at between 7.5 and 15 volume percent based on the total volume of the formulation.

The antigen content is best defined by the biological effect it provokes. Naturally, sufficient antigen should be present to provoke the production of measurable amounts of protective antibody. A convenient test for the biological activity of streptococcal organisms is set forth in U.S. Pat. No. 4,527,581 and involves the ability of the antigenic material undergoing testing to deplete a known positive antiserum of its protective antibody. The result is reported in the negative log of the $LD_{50}$ (lethal dose, 50%) for mice treated with virulent organisms which are pretreated with a known antiserum which itself was pretreated with various dilutions of the antigenic material being evaluated. A high value is therefore reflective of a high content of antigenic material which has tied up the antibodies in the known antiserum thus reducing or eliminating the effect of the antiserum on the virulent organism making a small dose lethal. It is preferred that the antigenic material present in the final formulation is at a level sufficient to increase the negative log of $LD_{50}$ by at least 1 preferably 1.4 compared to the result from the virulent organism treated with untreated antiserum. The absolute values obtained for the antiserum control and suitable vaccine material are, of course, dependent on the virulent organism and antiserum standards selected.

The vaccine formulation may be applied to the lymphatic tissue of the nose in any convenient manner. However, it is preferred to apply it as a liquid stream or liquid droplets to the walls of the nasal passage. This can advantageously be accomplished by using a small diameter tube which is sealed at its distal end with several holes in its side wall near the sealed end and which is fed at its proximal end by a dosing device such as a syringe. Inserting this tube into the horse's nose about 6 to 10 inches applies the vaccine formulation in the correct locale without concern about it by-passing the critical tissue. A particularly useful tube is about one millimeter in diameter with three or four one half millimeter holes in its circumference near its sealed end. Forcing liquid through such holes makes the liquid stream or large droplets particularly useful in the practice of this invention. Such a technique allows convenient field treatment without the need for special precautions or sedation of the horse being treated. Typically the horse's head is tilted back so the liquid can run down the nasal wall to the tonsilor tissue.

The vaccine formulation may be applied in any convenient dose so long as a sufficient amount of antigenic material (enough to increase the negative log of $LD_{50}$ in the test described hereinabove) is applied. However, it is preferred that the concentration of antigenic material is such that a dose between about 1 and 4 milliliters may be utilized.

The intranasal route may be used alone or in combination with other techniques. A particularly interesting regimen is a intramuscular injection followed by one or more intranasal administrations. The same formulation may be used for both routes or a separate formulation may be used for each, e.g. an adjuvanted formulation for the injection and a straight sterile water formulation for the nasal route.

Adequate protection may require more than one administration of vaccine. The number and timing of administration which is optimum for a given formulation can be readily determined by routine experimentation by one skilled in the art. In the case of Group C Streptococcal organisms an interval of between about 7 and 28 days with between two and three administrations is suitable. In the case of *Streptococcus equi* a three dose regimen at three week intervals has been found to be particularly suitable, especially when the first dose is an intramuscular injection and the two boosters are administered intranasally.

The invention is further illustrated, but is not intended to be limited by the following examples in which all parts and percentages are by weight unless otherwise specified.

EXAMPLES

Example 1

A vaccine was prepared from a four hour culture of *Streptococcus equi* grown in Todd Hewitt broth at 37° C. and at a pH of 7.2. Cells were separated from the growth medium, washed with 0.85 weight percent NaCl aqueous solution and resuspended in 0.85 weight percent NaCl aqueous solution. This cell suspension was autoclaved for 15 minutes at 121° C. and 15 psi. Subsequently 10 volume percent of an adjuvant based on polyacrylic acid crosslinked with polyallyl sucrose (commercially available as Carbopol 934P) combined with a mixture of polyoxyethylene sorbitan monooleate, sorbitan monolaurate, cottonseed oil and water as taught in U.S. Pat. No. 3,919,411 was added to the formulation.

This vaccine was used to immunize two horses intramuscularly and three horses intranasally. Two administrations of a 2 milliliter dose four weeks apart were used for both routes.

These five horses and a control horse were challenged intranasally three weeks after the second vaccine administration with 10 milliliters of a log phase culture of virulent *Streptococcus equi* (approximately $10^8$ organisms per milliliter). The intranasally vaccinated horses displayed a 56% reduction in clinical symptoms and the intramuscularly vaccinated horses displayed a 46% reduction in clinical symptoms compared to the control horse.

The sera of the horses vaccinated by both routes displayed a neutralizing effect on virulent *Streptococcus equi*. In particular they decreased the negative log (or increased the absolute value) of the $LD_{50}$ for mice treated with various dilutions of virulent organisms pretreated with the sera of the vaccinated horses as described in U.S. Pat. No. 4,529,582 as follows:

| Vaccination Route | At Vaccin-ation | Negative Log of $LD_{50}$ 4 Weeks post Vaccination | 7 Weeks post Vaccination |
|---|---|---|---|
| Intramuscular | 6.5 | 4.5 | 3.9 |
| Intranasal | 6.3 | 5.7 | 5.1 |

Example 2

A vaccine was prepared from a five hour culture of *Streptococcus equi* grown in the chemically defined medium (CDM) described in the article by I. Van de Rijn at pages 444 to 448 of Volume 27 (1980) of *Infection and Immunity* at 37° C. The cells were separated from the growth medium, washed with a 0.85 weight percent aqueous solution of sodium chloride and resuspended in a 0.85 weight percent aqueous solution of sodium chloride. This suspension was heated for 60 minutes at 65° C. A portion was then mixed with a sufficient amount of the adjuvant described in Example 1 to give a 10 volume percent content of adjuvant. Another portion was diluted in sterile buffered water at 1 part antigen source to 25 parts water and this diluted formulation was combined with a sufficient amount of the adjuvant of Example 1 to give a final content of 10 volume percent.

Three horses were vaccinated intramuscularly (IM) and four horses were vaccinated intranasally (IN) with the full strength vaccine and four horses were vaccinated intramuscularly (IM) with the diluted vaccine. The intramuscular administrations occurred twice, four weeks apart, while the intranasal administrations occurred four times at three weeks, four weeks and seven weeks after the initial vaccination. The dose for both administration routes was 2 milliliters.

These eleven horses and a control horse were challenged intranasally about ten weeks after the initial vaccination with 10 milliliters of a log phase culture of virulent Streptococcus equi (approximately $10^8$ organisms per milliliter). The intranasal and intramuscular administrations of full strength vaccine resulted in an about 40% reduction in clinical signs compared to the control horse while the intramuscular administration of diluted vaccine resulted in a 20% reduction.

The sera of all the vaccinated horses displayed some neutralizing effect on virulent Streptococcus equi as measured by the increase in the $LD_{50}$ for mice in accordance with U.S. Pat. No. 4,529,582.

The values of the negative log of the $LD_{50}$ for these treatments were as follows:

| Vaccine and Route | Negative Log of $LD_{50}$ at Various Numbers of Weeks After Vaccination | | | | | |
|---|---|---|---|---|---|---|
| | 0 | 2 | 4 | 6 | 7 | 10 |
| Undiluted IM | 6.1 | 5.7 | 5.8 | 5.7 | 5.8 | 4.4 |
| Undiluted IN | 6.9 | 6.7 | 6.3 | 6.3 | 6.7 | 6.1 |
| Diluted IM | 5.9 | 5.4 | 5.5 | 5.0 | 5.6 | 5.5 |

Thus, the intranasal route gives a symptomatic effect equivalent to the intramuscular administration of undiluted vaccine but a serological effect more closely aligned with intramuscular administration of the 1:25 dilution. This is some evidence that serological effect may not correlate directly with protection.

EXAMPLE 3

A. Vaccine Preparation

A lot of immuno-stimulating enzyme/anionic detergent extract of a culture of Streptococcus equi grown in the same chemically defined medium as Example 2 was prepared in accordance with the teachings of U.S. Pat. No. 4,582,798. The potency of this material was evaluated in accordance with the teachings of U.S. Pat. No. 4,529,581 and found to be within the range that correlates with field protection. In particular, the extract was prepared by sequential treatment at 37° C. with 5 units per milliliter of original culture volume of mutanolysin for about 16 hours followed with 0.05 weight percent of sodium dodecyl sulfate for about one half hour to give a preparation with a combining power of 7.0 or more measured as the negative log of $LD_{50}$ in mice of virulent organism treated with antiserum from a convalescent horse which antiserum was pretreated with this preparation. This preparation was used as the basis for the following five formulations:

(1) 0.5 weight percent of a hydroxylethylcellulose (HEC) ethoxylated with about 2.5 moles of ethylene oxide per mole of anhydroglucose unit with a viscosity of between 4500 and 6500 cps as a 2 weight percent aqueous solution and 2 volume percent of methyl salicylate were added to the extract preparation.

(2) 0.5 weight percent of the same HEC and 5.0 volume percent of dimethyl sulfoxide were added to the extract preparation.

(3) 0.5 weight percent of the same HEC and 2.0 weight percent of sodium glycoholate were added to the extract preparation.

(4) A sufficient amount of the adjuvant described in Example 1 was added to the extract preparation to constitute 10 percent by volume of the final formulation.

(5) The neat extract preparation.

B. Animal Selection

Fifty-three horses of mixed sex and breed located on three local farms were used in the trial. Horses were screened for seronegativity using the Passive Mouse Protection Assay (described in U.S. Pat. No. 4,528,582). It was not possible to obtain all seronegative animals and horses were assigned to six groups for the vaccination/challenge trial based upon two criteria:

(1) The mean titers of each of the six groups of horses should be approximately equal. Mean titers of the various groups ranged from 5.9 to 6.1 following assignment of animals.

(2) Each of the six groups of horses should contain a representative number of animals from all three farms.

Horses were vaccinated on the representative farms. At the time of challenge, all animals were transferred to a research farm where they were intranasally injected with virulent S. equi. At the request of the owners, horses from the three respective farms were not commingled post-challenge.

C. Vaccination Regimen

Five groups of horses (n=8 to 9) were vaccinated two or three times with 2.0 ml doses of intranasal, intramuscular, or topical formulations of S. equi Bacterial Extract. A final group of horses was held as nonvaccinated controls. The various vaccines and vaccination regimens are summarized in Table 1.

D. Challenge Procedure

Two to three days prior to challenge (12-14 days post booster), all horses were transferred to the research farm for challenge. Horses were challenged intranasally with log phase S. equi culture. Approximately $10^7$ organisms were administered to each horse using a ten inch modified cat catheter. This catheter had about a one millimeter inner bore, was sealed at its distal end and contained 3 or 4 radial discharge ports near this distal end. Horses were individually observed every other day for 45 days post challenge.

E. Evaluation of Response to Challenge

As indicated above, observations were made on individually challenged horses over a 45 day post-challenge observation period. At each observation, rectal temperatures were recorded, blood samples were drawn for determination of white blood cell count, and horses were examined for clinical signs such as nasal discharge, abscess formation, depression, and anorexia.

The response of horses to challenge was measured using the clinical index described in Table 2. *Daily Clinical Scores (DSCs) were assigned to each challenged horse on each observation day for four different parameters: abscess formation ($DCS_A$), nasal discharge ($DCS_N$), temperature response ($DCS_T$), and white blood cell elevation ($DCS_W$).

To analyze group response progressively throughout the post challenge observation period, Daily Group Clinical Indices (DGCIs) were calculated. The index measured group response on individual days throughout the 45 day observation period. The DGCI for a given day post challenge was obtained by totaling $DCS_A$, $DCS_N DCS_T$, and $DCS_W$ for all horses in a group and dividing by the number of horses in that group:

$$DGCI = \frac{\Sigma\ DCS_A + DCS_N + DCS_T + DCS_W \text{ for All Horses in a Group}}{\text{Number of Horses in Group}}$$

Cumulative Clinical Scores (CCSs) were obtained on individual horses for each of the four parameters ($CCS_A$, $CCS_N$, $CCS_T$, $CCS_W$) by totaling the daily clinical scores for the respective parameters over 45 days post challenge. The general formula for calculation of CCS values is as follows:

$$CCS_x = \Sigma\ DCS_x \text{ for 45 days post challenge}$$
(where $x = A, N, T,$ or $W$)

Individual Clinical Indices (ICIs) were obtained for each challenged horse by totaling $CCS_A$, $CCS_N$, $CCS_T$, $ICI = CCS_A + CCS_N + CCS_T + CCS_W$ The ICI constitutes a measure of individual horse response to challenge over the entire 45 day observation period.

The daily clinical scores were also used to analyze data on a group basis. *Specific Group Clinical Indices (SGCIs)* for abscess formation ($SGCI_A$), nasal discharge ($SGCI_N$), temperature response ($SGCI_T$), and WBC elevation ($SGCI_W$) were obtained by totaling $CCS_A$, $CCS_N$, $CCS_T$ or $CCS_W$ for all horses in a group and dividing by the number of horses in that group. The general formula for calculation of SGCI values is as follows:

$$SGCI_x = \frac{\Sigma\ CCS_x \text{ for All Horses in a Group}}{\text{Number of Horses in Group}}$$

The Specific Group Clinical Indices provide a measure of group response to challenge with respect to either abscess formation, nasal discharge, temperature, or WBC elevation.

Ultimately, a *Total Group Clinical Index (TGCI)* representative of overall response to challenge by a given group of horses was calculated by totaling $SGCI_A$, $SGCI_N$, $SGCI_T$, and $SGCI_W$: $TGCI = SGCI_A + SGCI_N + SGCI_T + SGCI_W$

F. Serological Testing

Sera was obtained from all horses used in the study prior to assignment into groups, prior to each vaccination, and again prior to challenge. Sera was tested using the Passive Mouse Protection Assay described in U.S. Pat. No. 4,529,582.

TABLE 1

S. equi vaccination/Challenge Trial Vaccination Protocol

| Group | Product | Application | Formulation | Dose | Regimen | # Horses |
|---|---|---|---|---|---|---|
| A | S. equi Bacterial Extract | Intranasal | 2.0% methyl salicylate, 0.5% hydroxyethylcellulose | 2.0 ml | 3 doses, 3 weeks apart | n = 8 |
| B | S. equi Bacterial Extract | Intranasal | 5.0% DMSO, 0.5% hydroxyethylcellulose | 2.0 ml | 3 doses, 3 weeks apart | n = 9 |
| C | S. equi Bacterial Extract | (1) Intramuscular (2) Intranasal | (1) 10% Adjuvant of Example 1 (2) No additives | 2.0 ml 2.0 ml | 3 doses, 3 weeks apart | n = 9 |
| D | S. equi Bacterial Extract | Topical | 2.0% sodium glycocholate 0.5% hydroxyethylcellulose | 2.0 ml | 3 doses, 3 weeks apart | n = 9 |
| E | S. equi Bacterial Extract | Intramuscular | 10% Adjuvant of Example 1 | 2.0 ml | 2 doses, 3 weeks apart | n = 9 |
| F | Nonvaccinated Controls | N/A | N/A | N/A | N/A | n = 9 |

TABLE 2

| CLINICAL SIGN | NUMBER OF POINTS |
|---|---|
| *Streptococcus equi* Clinical Index | |
| *Abscess formation | 20 |
| **Abscess duration | 20 |
| Rectal Temperatures (°F.) | |
| <102.0 | 0 |
| 102.0–102.4 | 1 |
| 102.5–103.9 | 2 |
| ≧104.0 | 5 |
| White Blood Cell Counts | |
| >50% increase | 0 |
| 50–99% increase | 2 |
| >100% increase | 5 |
| Nasal Discharge | |
| None to Slight Discharge | 0 |
| Moderate Discharge | 5 |
| Heavy Discharge | 10 |

*Abscess formation refers to the first day abscesses become visible.
**Abscess duration refers to all subsequent days abscesses are visible prior to draining.

III. RESULTS

Post-challenge clinical observations on six groups of challenged horses are summarized in Table 3 and in FIGS. 1 through 6. Table 3 presents Specific Group Clinical indices (SGCIs) and Total Group Clinical Indices (TGCIs) for five groups of vaccinates and one group of nonvaccinated controls. FIG. 1 is a bar graph comparing TGCIs of all vaccinate and control groups of horses. FIGS. 2 through 6 compare the Daily Group Clinical Indices (DGCIs) of individual vaccination groups with those of control horses.

As shown in Table 3, two of five vaccination groups showed at least 70% reduction in total group clinical indices when compared with nonvaccinated controls. The two most efficacious treatments were Treatment B (DMSO intranasal vaccine) and Treatment C (Adjuvanted IM vaccine followed by two IN doses of nonadjuvanted extract). One additional intranasal treatment (Treatment A using methyl salicylate as a transdermal carrier) provided a reduction in TGCI. Horses vaccinated with other formulations, a topical treatment containing sodium glycoholate (Treatment D) and an intramuscular treatment (Treatment E, Strep. equi antigen with adjuvant) showed higher TGCIs than the control horses. However, this latter treatment (Strep. equi with adjuvant) delayed onset of disease by 14 to 18 days in relation to nonvaccinated control horses.

Specific group clinical indices (SGCIs) presented in Table 3 indicate that abscess formation (lymphadenopathy) is the most significant clinical sign appearing in unprotected vaccine groups and control horses.

FIGS. 2 through 6, comparing daily group clinical indices of vaccinated horses with controls, illustrate the relative effectiveness of Treatments B and C in relation to the less efficacious treatments. These graphs indicate that the two less efficacious treatments (A and E) did appear to delay onset of disease with respect to the control group.

Results of serological testing are shown in Table 4. This table presents mean mouse passive antibody titers obtained for the six groups of horses prior to group assignment, before each vaccination, and again prior to challenge. Included in the table is the net change in antibody titer (ΔMean Titer) from time of first vaccination until time of challenge. As would be expected, groups of horses vaccinated intramuscularly (Groups C and E) show relatively large changes in humoral antibody levels (note that increases in passive mouse antibody titers are actually decreases in the negative logs of the mouse $LD_{50}$ levels). Group E, showed an increase in mean titer $\geq 2.0$ log mouse $LD_{50}$. Horses receiving Treatment C (one IM dose followed by two IN doses) also showed a considerable 1.8 log increase in humoral antibody titer. In contrast, horses which received intranasal or topical vaccine showed only slight increase in titer, probably attributable to test variation. Since humoral antibody titers were highest in many of the least protected groups, one can surmise that these titers bear little or no relationship to actual protection.

An unexpected result of the trial was the death of three horses at four to six weeks post challenge in groups B, D, and E. All three animals developed internal abscesses adhering to the wall of the individual animals' rectum. Pure S. zooepidemicus was isolated from the lesions in two of the three horses. Although the autopsy showed the third horse to have an old abscess attached to the rectal wall immediately anterior to the anus, a mixture of unidentified bacteria was obtained from the lesion. Autopsy also showed this horse to be anemic and short of overall body fat. One additional horse in group B also developed a rectal abscess. However in this instance the abscess drained externally and the animal survived.

Only one of the three dead horses showed significant clinical response to challenge (i.e. nasal discharge or abscess formation) prior to death. For the purposes of data evaluation, clinical signs of the three horses were included in group analyses, (DGCI, TGCI) up to the day of their demise. Since deaths resulted from a factor not directly related to S. equi infection, no additional clinical index points were assigned.

TABLE 3

STREPTOCOCCUS EQUI HORSE CHALLENGE STUDY
SIX INTRANASAL, INTRAMUSCULAR, TOPICAL FORMULATIONS
CLINICAL RESPONSE OF CHALLENGE GROUPS
(SPECIFIC AND TOTAL GROUP CLINICAL INDICES)

| Group | Description | Dose/Route | Abscess Formation (SGCI$_A$) | Nasal Discharge (SGCI$_N$) | Temp. Elev. (SGCI$_T$) | WBC Elev. (SGCI$_W$) | Total Group Clinical Index (TGCI) | Percent Reduction in TGCI (vs. Controls) |
|---|---|---|---|---|---|---|---|---|
| A | Methyl Salicylate plus HEC* | 3 Intranasal (2.0 ml) | 5.0 | 3.1 | 3.9 | 4.5 | 16.5 | 34.3% |
| B | DMSO plus HEC* | 3 Intranasal (2.0 ml) | 0 | 1.1 | 3.0 | 1.7 | 5.8 | 76.9% |
| C | Adjuvant No additives | 1 Intramuscular 2 Intranasal (2.0 ml) | 0 | 1.7 | 2.4 | 2.0 | 6.1 | 75.7% |
| D | Sodium glycoholate plus HEC* | 3 Topical (2.0 ml) | 24.4 | 10.0 | 2.0 | 0 | 36.4 | 0% |
| E | Adjuvant | 2 Intramuscular (2.0 ml) | 31.1 | 5.0 | 3.7 | 3.8 | 43.6 | 0% |
| F | Unvaccinated Controls | N/A | 17.8 | 3.3 | 2.4 | 1.6 | 25.1 | N/A |

*HEC = Hydroxyethylcellulose

TABLE 4

STREPTOCOCCUS EQUI HORSE CHALLENGE STUDY:
SIX INTRANASAL, INTRAMUSCULAR, TOPICAL FORMULATIONS
GROUP SEROLOGICAL RESPONSE
MEAN MOUSE PASSIVE ANTIBODY TITERS*

| Group | Description | Dose/Route | Prescreen | Pre-vacc. | Pre-Booster | Pre 2nd Booster | Prechallenge | Δ Mean Titer** |
|---|---|---|---|---|---|---|---|---|
| A (n = 8) | Methyl Salicylate plus HEC*** | 3 Intranasal (2.0 ml) | 5.9 | 5.5 | 5.4 | 5.2 | 5.2 | 0.3 |

TABLE 4-continued
STREPTOCOCCUS EQUI HORSE CHALLENGE STUDY:
SIX INTRANASAL, INTRAMUSCULAR, TOPICAL FORMULATIONS
GROUP SEROLOGICAL RESPONSE
MEAN MOUSE PASSIVE ANTIBODY TITERS*

| Group | Description | Dose/Route | Prescreen | Pre-vacc. | Pre-Booster | Pre 2nd Booster | Prechallenge | Δ Mean Titer** |
|---|---|---|---|---|---|---|---|---|
| B (n = 9) | DMSO plus HEC*** | 3 Intranasal (2.0 ml) | 5.9 | 6.1 | 6.1 | 6.0 | 5.8 | 0.3 |
| C (n = 9) | Adjuvant No Additives | 1 Intramuscular 2 Intranasal (2.0 ml) | 6.0 | 6.6 | 4.2 | 5.0 | 4.8 | 1.8 |
| D (n = 9) | Sodium glycoholate plus HEC*** | 3 Topical (2.0 ml) | 6.0 | 5.9 | 5.7 | 6.1 | 5.4 | 0.5 |
| E (n = 9) | Adjuvant | 2 Intramuscular (2.0 ml) | 6.0 | 6.8 | 4.4 | N/A | 3.6 | 3.2 |
| F (n = 9) | Unvaccinated Controls | N/A | 5.9 | 5.4 | 5.8 | N/A | 4.7 | 0.7 |

*Mean Titer is the average of the log mouse $LD_{50}$s obtained when horse sera are tested using the Passive Mouse Protection Assay described in U.S. Pat. No. 4,529,582.
**Δ Mean Titer is the numerical difference between prechallenge and prevaccination titers.
***HEC = Hydroxyethylcellulose with a room temperature viscosity as a 2 weight percent solution of between 4500 and 6500 cps.

IV. EVALUATION

Results of this experiment indicate that an intranasally administered *S. equi* bacterial extract can protect horses from experimental challenge. The three dose IN Treatment with the DMSO containing formulation reduced total clinical signs by 76.9% when compared to nonvaccinated control horses. Also appearing particularly efficacious in this trial was a three dose regimen consisting of one IM dose of adjuvanted vaccine, followed by two IN doses of nonadjuvanted antigen extract.

Although strongly positive results were seen with the two previously described formulations, unexpectedly poor results were seen with Treatment E, representative of the 2 ml STREPGUARD product presently licensed by USDA. This vaccine formulation had been previously shown to be efficacious in a challenge study employing 59 horses. One reason for the differing results could relate to the method of challenge. In the earlier trial, challenge was largely indirect (horses were brought into an endemic area and virulent *S. equi* was applied only to the muzzle of each animal). In the current trial, *S. equi* organisms were injected directly into the nasal passages. It is possible that the second challenge method can "overwhelm" the intramuscular product. The fact the Treatment E did delay onset of disease in vaccinated horses may provide indirect support for this conclusion. One would not expect the intramuscular vaccine to stimulate much local secretory response. In actuality, this result may provide evidence of the need for an intranasally administered product to stimulate local IgA and provide stronger local immunity.

The fact that humoral antibody titers, as measured by the mouse passive antibody test, do not relate to protection is not particularly surprising. A similar result was seen in an earlier challenge trial with *S. equi* Bacterial Extract. It seems likely that protection against experimental *S. equi* challenge involves a local mechanism operating at the level of the nasal mucosa.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process of immunizing horses against infection by *Streptococcus equi* comprising applying inactivated organisms, antigenic extracts, or recombinant DNA or synthetic peptide antigens of *Streptococcus equi* to the nasal mucosa or tonsilor tissue of said horses in a dose sufficient to increase the negative log of $LD_{50}$.

2. The process of claim 1 wherein the antigenic material is incorporated into a liquid carrier and sprayed onto the walls of the nose in the vicinity of the tonsilor tissue as a liquid stream or large droplets.

3. The process of claim 2 wherein the liquid carrier also contains a transdermal penetrant.

4. The process of claim 3 wherein the transdermal penetrant is either dimethyl sulfoxide or methyl salicylate.

5. The process of claim 2 wherein the liquid carrier also contains a thickening agent.

6. The process of claim 5 wherein the thickening agent is cellulose based.

7. The process of claim 6 wherein the thickening agent is hydroxyethylcellulose.

8. The process of claim 5 wherein the liquid carrier also contains a transdermal penetrant.

9. The process of claim 8 wherein
(a) the liquid carrier is water, and
(b) the thickening agent is cellulose based.

10. The process of claim 9 wherein
(a) the transdermal penetrant is dimethyl sulfoxide or methyl salicylate, and
(b) the thickening agent is hydroxyethylcellulose.

11. The process of claim 1 in which the antigenic material is an enzyme extract of *Streptococcus equi.*

12. A process of immunizing horses against respiratory infection by *Streptococcus equi* comprising
(a) an intramuscular injection of said horses with a vaccine based on killed organisms, antigenic extracts or recombinant DNA or synthetic peptide antigens of *Streptococcus equi,* and
(b) an intranasal application of said horses with a vaccine based on killed organisms, antigenic extracts or recombinant DNA or synthetic peptide antigens of *Streptococcus equi* in a dose sufficient to increase the negative log of $LD_{50}$.

13. The process of claim 12 wherein the intranasally applied vaccine includes a liquid carrier and is sprayed onto the walls of the horse's nose in the vicinity of the tonsilor tissue as a liquid stream or large droplets.

14. The process of claim 13 wherein the liquid carrier is sterile water and the injected vaccine contains an adjuvant.

15. The process of claim 14 wherein the intranasal vaccine is free of adjuvant.

16. The process of claim 12 wherein
    (a) the injected vaccine contains an adjuvant,
    (b) the intranasal vaccine carrier comprises water and is sprayed onto the walls of the horse's nose in the vicinity of the tonsilor tissue as a liquid stream or large droplets, and
    (c) the antigenic material in both vaccines is an enzyme extract.

17. A process of immunizing horses against the respiratory invasion of *Streptococcus equi* comprising
    (a) preparing a waterborne antigenic enzyme and detergent extract of *Streptococcus equi* which displays a combining power value of at least about four in the mouse combining power test,
    (b) adding between about 0.25 and 1 weight % of hydroxyethylcellulose and between about 2.5 and 10 weight % of dimethyl sulfoxide, based on the total formulation, to the waterborne extract,
    (c) applying between about 1 and 3 milliliters of this formulation to the nasal tonsilor tissue of the horse by spraying it as a liquid stream or large droplets on the interior nasal wall in the vicinity of this tissue in a dose sufficient to increase the negative log of $LD_{50}$, and
    (d) repeating the application in between about one (1) and four (4) weeks of the initial application.

18. The process of claim 17 wherein the formulation is applied by inserting a small diameter tube sealed at its distal end and with circumferential holes near this end into the horse's nose in the vicinity of the tonsilor tissue and passing the formulation through this tube.

19. The process of claim 17 wherein the horse's head is tilted back, and the tube is inserted in no farther than the beginning of the tonsilor tissue so that the applied formulation can flow along the nasal wall under the influence of gravity to this tissue.

* * * * *